United States Patent
Prevot et al.

(10) Patent No.: US 11,497,610 B2
(45) Date of Patent: Nov. 15, 2022

(54) STEM FOR A HIP PROSTHESIS, WITH FIXED OR MODULAR NECK

(71) Applicant: ADLER ORTHO S.P.A., Cormano (IT)

(72) Inventors: Nicolas Prevot, Bordeaux (FR); Pierre Bruneteau, Seignosse (FR); Nicolas Reina, Balma (FR); Jean-François Gonzalez, Toulon (FR); Cesare Faldini, Pianoro (IT); Francesco Traina, Ferrara (IT); Frederic Mouilhade, Rouen (FR); Sebastian Dawson Bowling, Sussex (GB)

(73) Assignee: ADLER ORTHO S.P.A., Cormano (IT)

( * ) Notice: Subject to any disclaimer, the term of this patent is extended or adjusted under 35 U.S.C. 154(b) by 0 days.

(21) Appl. No.: 17/292,550

(22) PCT Filed: Aug. 6, 2019

(86) PCT No.: PCT/EP2019/071153
§ 371 (c)(1),
(2) Date: May 10, 2021

(87) PCT Pub. No.: WO2020/094269
PCT Pub. Date: May 14, 2020

(65) Prior Publication Data
US 2022/0000624 A1    Jan. 6, 2022

(30) Foreign Application Priority Data

Nov. 9, 2018   (IT) ................... 102018000010188

(51) Int. Cl.
*A61F 2/30*     (2006.01)
*B33Y 10/00*    (2015.01)
*A61F 2/36*     (2006.01)

(52) U.S. Cl.
CPC ...... *A61F 2/30942* (2013.01); *A61F 2/30771* (2013.01); *A61F 2/367* (2013.01);
(Continued)

(58) Field of Classification Search
CPC .. A61F 2/30942; A61F 2/30771; A61F 2/367; A61F 2/3676; A61F 2002/30011;
(Continued)

(56) References Cited

U.S. PATENT DOCUMENTS

| | | | | |
|---|---|---|---|---|
| 4,623,349 A | * | 11/1986 | Lord | A61F 2/3662 623/23.44 |
| 4,695,283 A | * | 9/1987 | Aldinger | A61F 2/30942 623/23.24 |

(Continued)

FOREIGN PATENT DOCUMENTS

| | | |
|---|---|---|
| AU | 2006200192 A1 | 2/2006 |
| WO | 9200046 A1 | 1/1992 |

(Continued)

OTHER PUBLICATIONS

International Search Report dated Oct. 22, 2019 re: Application No. PCT/EP2019/071153, pp. 1-3, citing: WO 2012/034771 A1, AU 2006 200 192 A1, WO 2013/155500 A1 and WO 92/00046 A1.

(Continued)

*Primary Examiner* — Yashita Sharma
*Assistant Examiner* — Melissa A Hoban
(74) *Attorney, Agent, or Firm* — Cantor Colburn LLP

(57) ABSTRACT

A stem for a hip prosthesis, with fixed or modular neck, which includes a stem body divided into a proximal region and a distal region, the body of the stem forming an anterior wall, a posterior wall, a medial wall, and a lateral wall. The anterior wall, the posterior wall, and the medial wall are (Continued)

provided at least partially with a porous structure with undercuts, the lateral wall being provided with a machining allowance.

8 Claims, 7 Drawing Sheets

(52) U.S. Cl.
CPC ......... *A61F 2/3662* (2013.01); *A61F 2/3676* (2013.01); *B33Y 10/00* (2014.12); *A61F 2002/30011* (2013.01); *A61F 2002/3093* (2013.01); *A61F 2002/3096* (2013.01); *A61F 2002/30322* (2013.01); *A61F 2002/30604* (2013.01); *A61F 2002/30784* (2013.01); *A61F 2002/30985* (2013.01)

(58) Field of Classification Search
CPC .. A61F 2002/30322; A61F 2002/30604; A61F 2002/30784; A61F 2002/3093; A61F 2002/3096; A61F 2002/30985
See application file for complete search history.

(56) References Cited

U.S. PATENT DOCUMENTS

| | | | | |
|---|---|---|---|---|
| 5,725,586 | A * | 3/1998 | Sommerich | A61F 2/30734 623/23.35 |
| 6,911,100 | B1 * | 6/2005 | Gibbs | C21D 7/02 148/668 |
| 2004/0099983 | A1 * | 5/2004 | Dirscherl | B22F 10/10 264/162 |
| 2004/0102854 | A1 * | 5/2004 | Zhu | A61F 2/367 623/23.15 |
| 2004/0148033 | A1 * | 7/2004 | Schroeder | B24C 1/10 623/23.53 |
| 2006/0002810 | A1 * | 1/2006 | Grohowski | B22F 3/1025 419/2 |
| 2006/0263233 | A1 * | 11/2006 | Gardinier | A61L 27/306 419/11 |
| 2007/0202351 | A1 * | 8/2007 | Justin | A61L 27/306 428/660 |
| 2007/0287027 | A1 * | 12/2007 | Justin | A61L 27/54 428/666 |
| 2008/0033568 | A1 * | 2/2008 | Link | A61F 2/30767 623/22.4 |
| 2008/0243264 | A1 * | 10/2008 | Fonte | A61F 2/30942 623/22.43 |
| 2010/0094420 | A1 * | 4/2010 | Grohowski, Jr. | B22F 7/002 623/16.11 |
| 2012/0265319 | A1 * | 10/2012 | Prybyla | A61F 2/34 623/22.36 |
| 2015/0173908 | A1 * | 6/2015 | Shimozono | A61F 2/3672 623/20.36 |
| 2017/0071744 | A1 * | 3/2017 | Bali | A61L 27/06 |
| 2018/0000598 | A1 * | 1/2018 | Amis | A61F 2/3662 |
| 2018/0228616 | A1 * | 8/2018 | Piecuch | A61F 2/30942 |
| 2019/0283324 | A1 * | 9/2019 | Tarumi | B23C 3/12 |
| 2021/0093460 | A1 * | 4/2021 | Satterthwaite | A61F 2/3609 |

FOREIGN PATENT DOCUMENTS

| | | |
|---|---|---|
| WO | 2012034771 A1 | 3/2012 |
| WO | 2013155500 A1 | 10/2013 |

OTHER PUBLICATIONS

IT Search Report dated Jul. 12, 2019 re: Application No. 2018000010188, pp. 1-7, citing: WO 2012/034771 A1, AU 2006 200 192 A1, WO 2013/155500 A1 and WO 92/00046 A1.
Written Opinion dated Oct. 22, 2019 re: Application No. PCT/EP2019/071153, pp. 1-6, citing: WO 2012/034771 A1, Au 2006 200 192 A1, WO 2013/155500 A1 and WO 92/00046 A1.

* cited by examiner

STEM FOR A HIP PROSTHESIS, WITH FIXED OR MODULAR NECK

TECHNICAL FIELD

The present disclosure relates to a stem for a hip prosthesis, with fixed or modular neck. More specifically, the disclosure relates to a stem for a hip prosthesis which is adapted to be accommodated in the medial-proximal part of the femur of a leg.

BACKGROUND

As is known, an artificial hip prosthesis is made up substantially of:
- a stem with a neck—fixed to the stem, or modular;
- a head, adapted to be arranged at the apex of the neck;
- an acetabulum with an insert inside which the above mentioned head rotates.

The stem is made to be accommodated in the medial-proximal part of the femur of a leg and can be long, medium or short.

The three types of stems have drawbacks and advantages. In particular, the long stem is difficult to insert into the medullary canal of the human femur (which presents curves along multiple axes), but once implanted it is stable.

The short stem is easy to implant as it remains in the more proximal spongier part of the bone, but it does not enter the medullary canal and therefore it may be positioned in an incorrect way.

The medium stem is a good compromise between the long stem and the short stem as it averages out the advantages and the shortcomings of the two stems mentioned above.

Hip stems, in order to be eligible for certification, are subjected to fatigue tests, which must be overcome in order to ensure that a stem offers optimal conditions of use.

Short stems undergo fatigue tests with not excessively high loads.

The weakest part of the hip stem, subjected to fatigue tests, is the lateral part where the fibers are extended (as a result of stresses) and where any small imperfection can trigger a crack that leads to the breakage of the stem.

SUMMARY

The aim of the present disclosure is to provide a stem for a hip prosthesis that is of the medium and/or long type, which overcomes the fatigue tests imposed by the regulations.

Within this aim, the present disclosure provides a stem for a hip prosthesis that has a lateral part of the stem, usually the weakest, which is capable of withstanding the above mentioned fatigue tests.

The present disclosure also provides a stem for a hip prosthesis that is obtained by way of additive manufacturing technology.

The present disclosure further provides a stem for a hip prosthesis that has a lateral surface that is substantially free from cracks.

The present disclosure also provides a stem for a hip prosthesis that is highly reliable, easily and practically implemented and of low cost.

This aim and these and other advantages which will become better apparent hereinafter are achieved by providing a stem for a hip prosthesis, with fixed or modular neck, which comprises a stem body which is divided into a proximal region and a distal region, the body of the stem forming an anterior wall, a posterior wall, a medial wall and a lateral wall, characterized in that the anterior wall, the posterior wall and the medial wall are provided at least partially with a porous structure with undercuts, said lateral wall being provided with a machining allowance.

BRIEF DESCRIPTION OF THE DRAWINGS

Further characteristics and advantages of the disclosure will become better apparent from the description of preferred, but not exclusive, embodiments of the stem for a hip prosthesis according to the present disclosure, which are illustrated by way of non-limiting example in the accompanying drawings wherein.

DETAILED DESCRIPTION OF THE DRAWINGS

Figure 5:
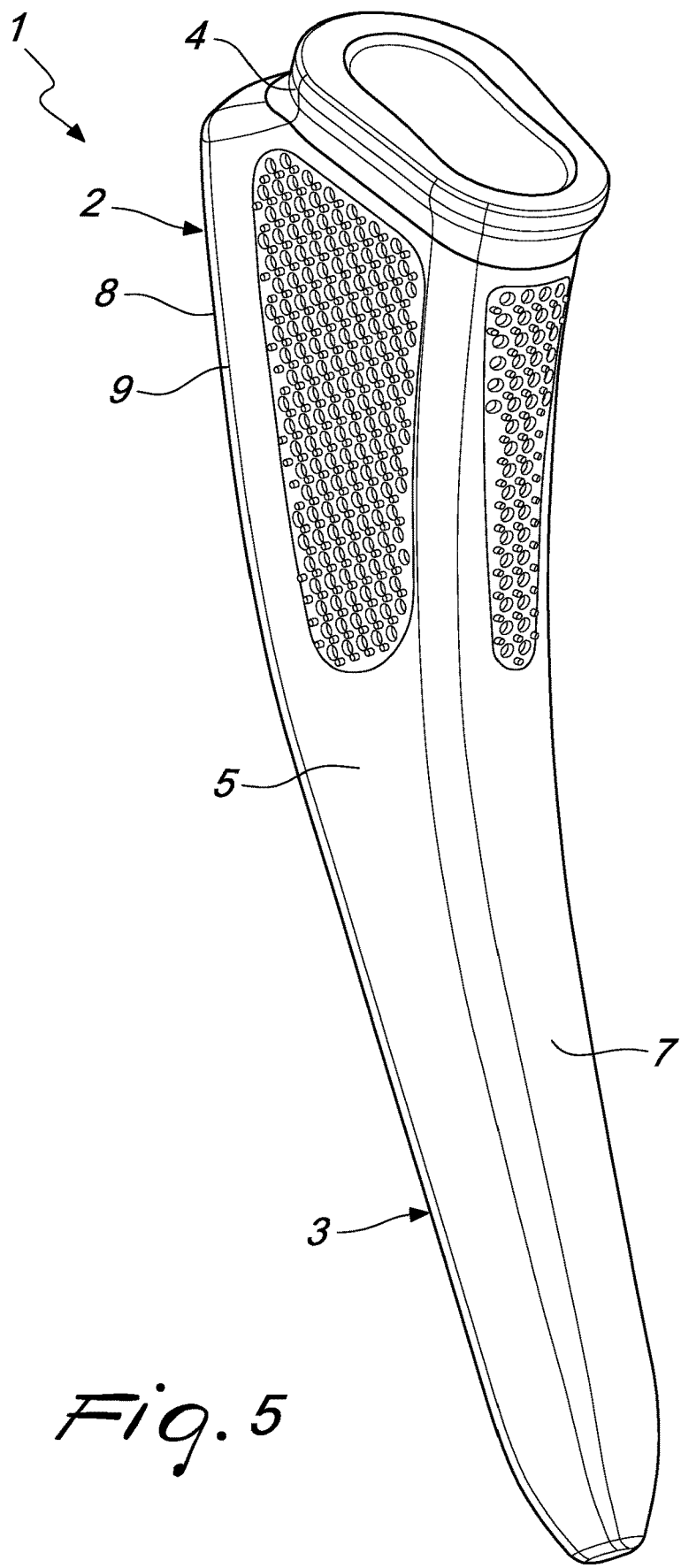
FIG. 5 is a perspective view of a second embodiment of the stem according to the disclosure.
Figure 6:
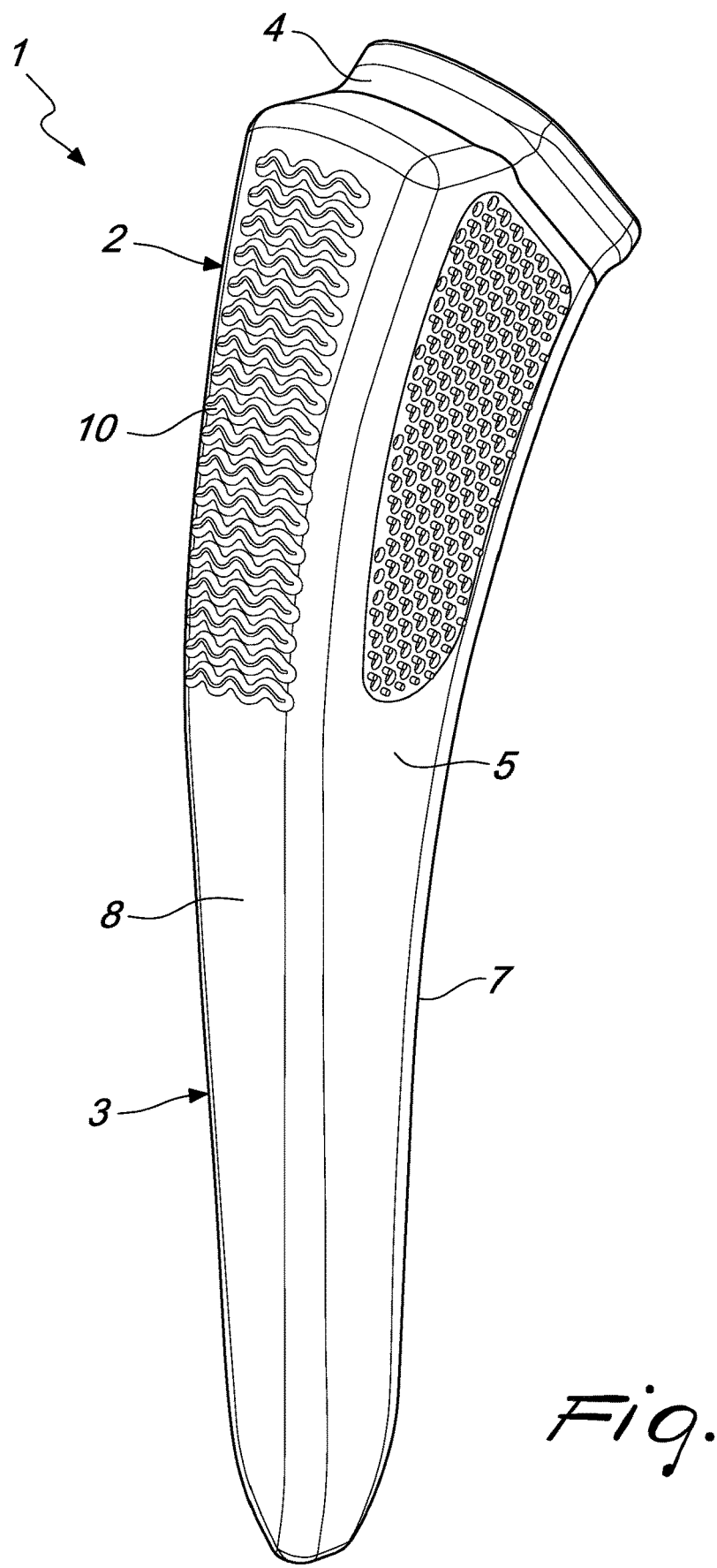
FIG. 6 is an additional perspective view of the stem in FIG. 5.
Figure 7:
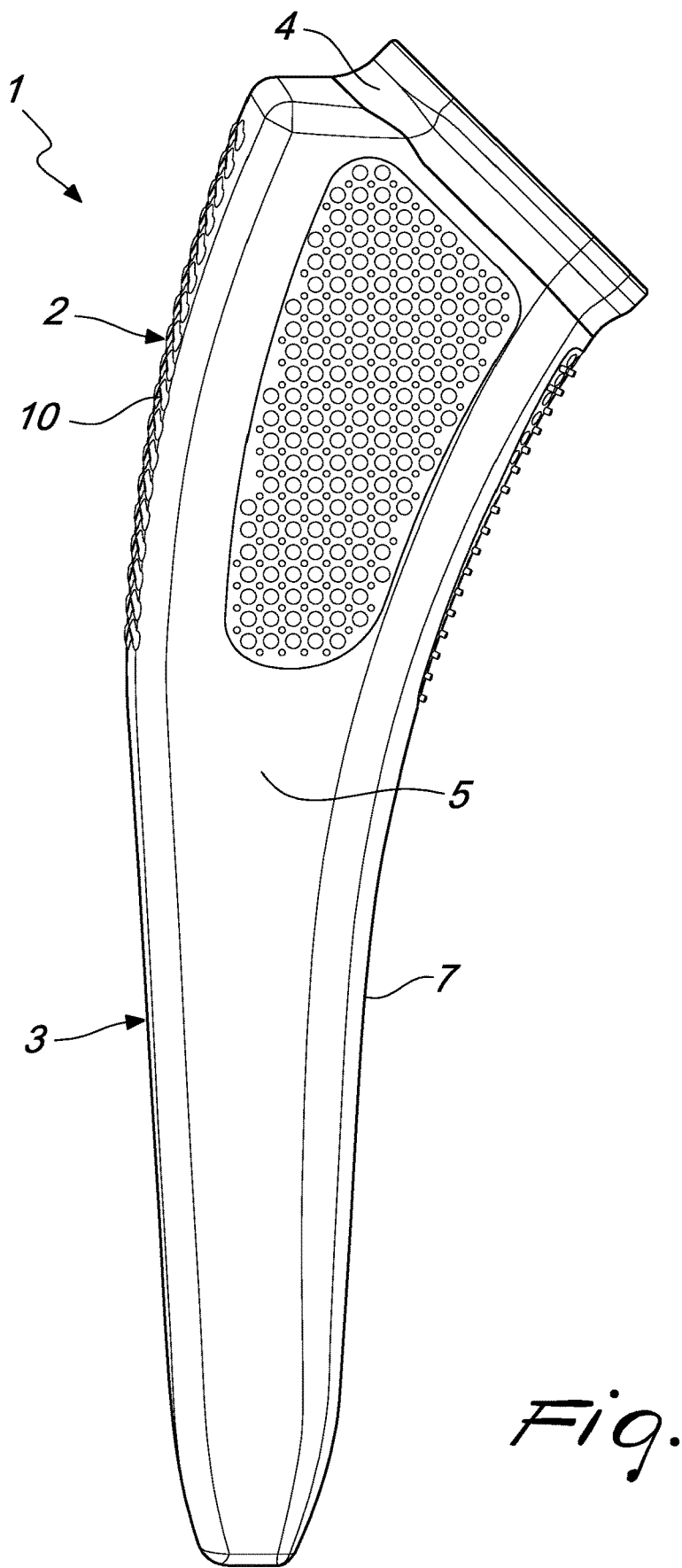
FIG. 7 is another additional perspective view of the stem in FIGS. 5 and 6.

With reference to the figures, the stem for a hip prosthesis, with fixed or modular neck (the first embodiment in FIGS. 1-4 refers to the stem with a fixed neck while the second embodiment in FIGS. 5-7 refers to the stem with a modular neck), according to the disclosure, generally designated by the reference numeral 1, has a proximal region 2 and a distal region 3. The proximal region 2 ends with a neck 4 to which a head can be attached. The neck 4 can be modular or fixed.

The proximal region 2 of the stem 1 has an anterior surface 5, a posterior surface 6, a medial surface 7 and a lateral surface 8. The anterior surface 5, the posterior surface 6 and the medial surface 7 are made at least partially with a porous structure with undercuts, advantageously with dimensions of the pores of from 300 to 1000 microns.

Conveniently, the lateral surface 8 of the stem 1 is made with a layer of machining allowance 9 in order to prevent the formation of cracks. The machining allowance 9 is then removed with machine tools until a smooth surface is obtained, with no porosity but with a relief pattern 10 that aids osseointegration (see FIG. 3).

Figure 1:
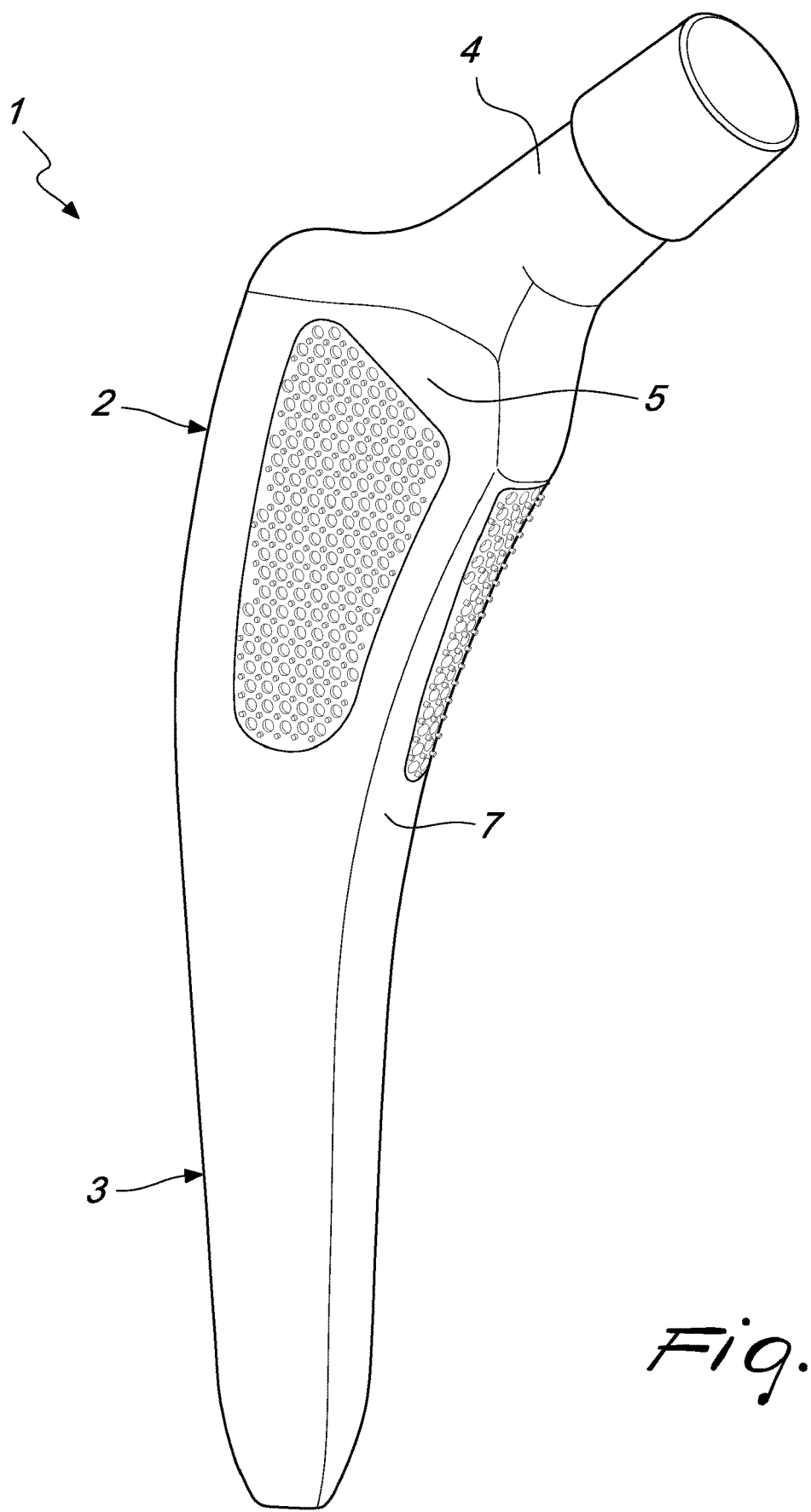
FIG. 1 is a first perspective view of the stem according to the disclosure.
Figure 2:
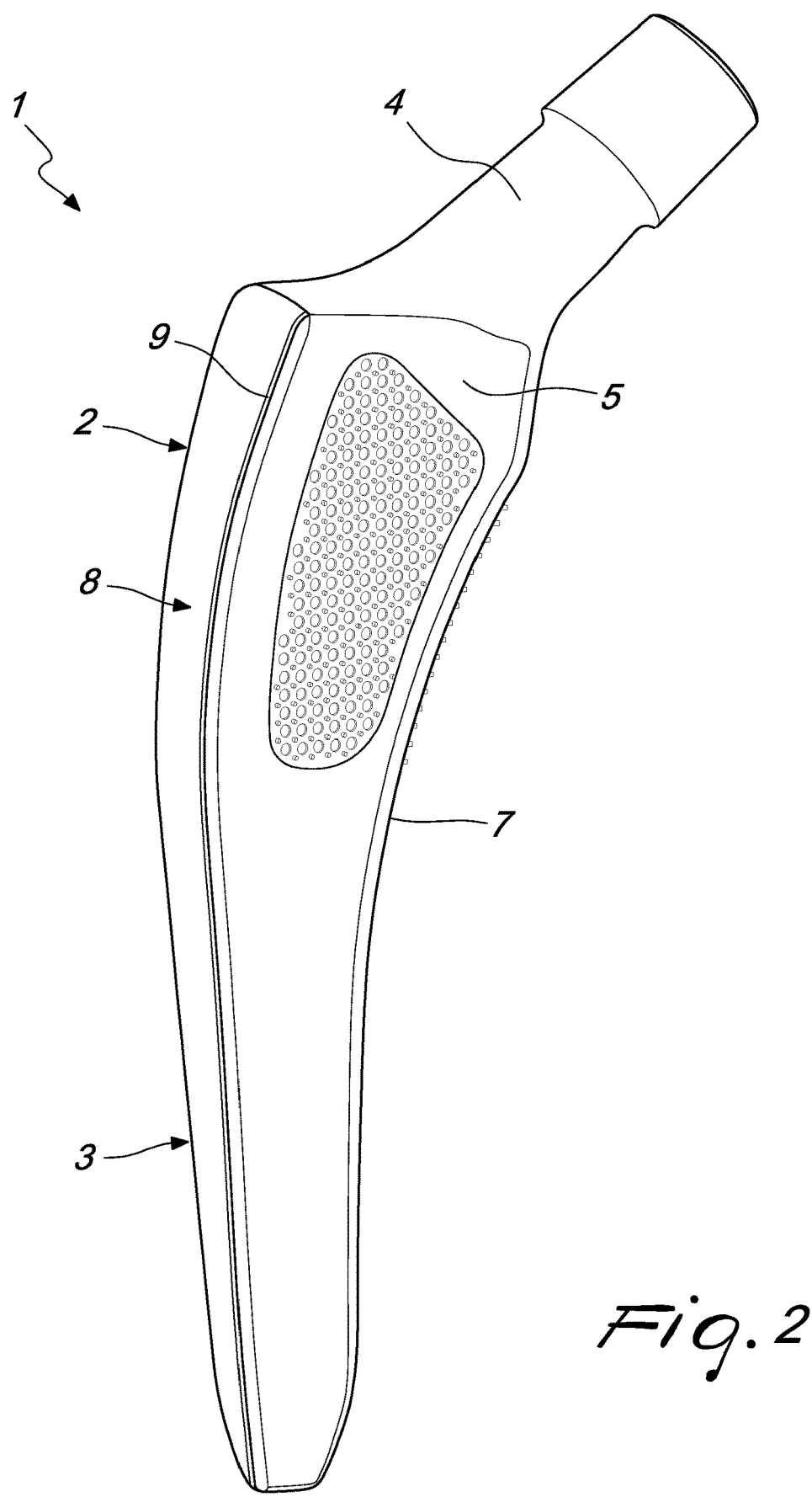
FIG. 2 is a second perspective view of the stem according to the disclosure, in an intermediate step of machining.
Figure 3:
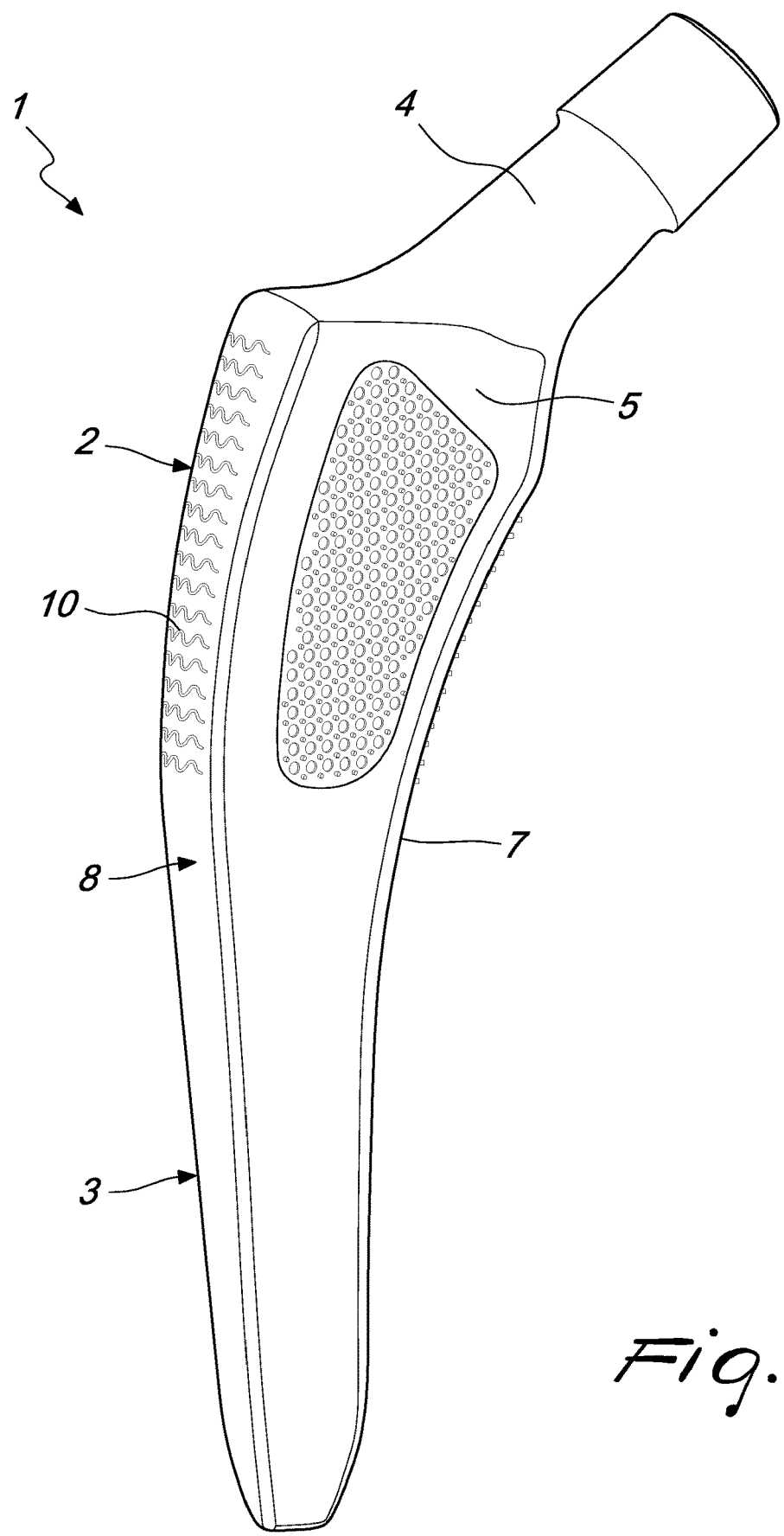
FIG. 3 is a second perspective view of the stem according to the disclosure, in the final configuration.
Figure 4:
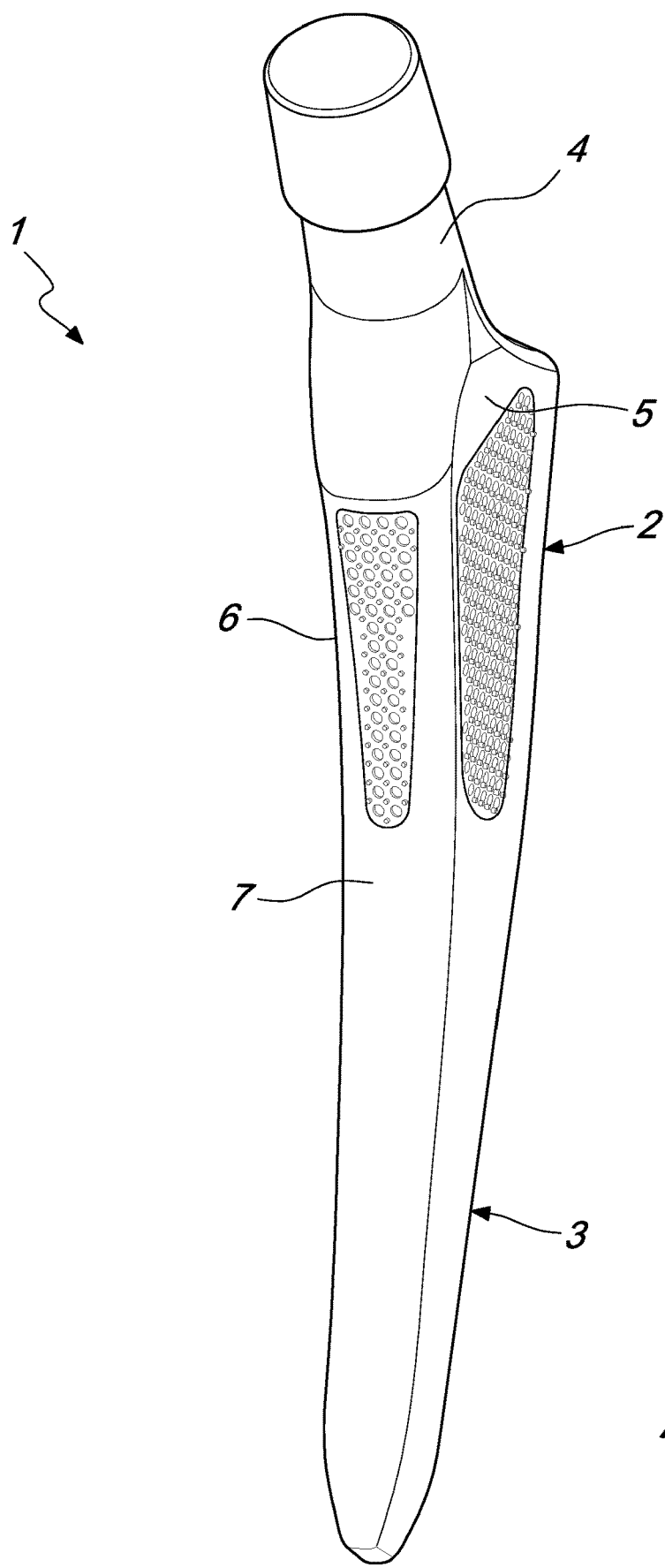
FIG. 4 is a third perspective view of the stem according to the disclosure.

The corrugated pattern shown in FIG. 3 is purely for the sake of example and it is to be understood that it may have any other form that makes it possible to improve osseointegration.

The step of removing the machining allowance 9 is carried out by partially removing the machining allowance at the proximal region 2, so as to obtain the relief pattern 10.

In a position below the relief pattern 10, i.e. substantially at the distal region 3, the machining allowance 9 is however removed completely.

After the step of machining with machine tools, a shot peening treatment is conveniently carried out, so as to increase the hardness of the material and accordingly the resistance to fatigue.

Prior to the step of machining with machine tools it is essential to carry out a HIP (Hot Isostatic Pressing) treatment in order to eliminate/reduce the internal porosities.

Given that the more superficial layers are more porous than the innermost layers, the HIP treatment offers the advantage of closing the porosity of the innermost layers (closed holes) which are already less porous than the superficial layers.

Considering that the surface porosities (open holes) are deformed and can even be widened as a result of the HIP treatment, the subsequent step of mechanical machining (carried out therefore after the HIP step) has the advantage of removing the more superficial layers where even after the HIP treatment there are open pores, thus making internal layers emerge which are already less porous to begin with and in which the porosity will subsequently be reduced by the HIP treatment.

The additive manufacturing technique is carried out in layers, and the stem can therefore be vertically-extended, i.e. with many layers of small dimensions on top of each other, or horizontally-extended, i.e. with a relatively small number of layers which have very long dimensions.

In this second case, the layer of machining allowance 9 can be provided so as to define a lateral surface 8 that is substantially flat, so as to provide an adequate resting surface.

The step of removing the machining allowance 9 will then make it possible to confer the desired curvature on the lateral surface 8.

The presence of machining allowance 9 at the lateral surface 8 of the stem of the hip prosthesis makes it possible to avoid the formation of cracks.

Conveniently, the stem is made of titanium alloy or another material suitable for the purpose.

In practice it has been found that the stem for a hip prosthesis according to the present disclosure fully achieves the set aim and advantages, in that it can be used with additive manufacturing technology, with a lateral wall with a machining allowance in order to avoid the formation of cracks, the stem therefore being capable of passing the fatigue tests with heavier loads and therefore being capable of being made in medium and/or long sizes as well.

The stem, thus conceived, is susceptible of numerous modifications and variations, all of which are within the scope of the appended claims.

Moreover, all the details may be substituted by other, technically equivalent elements.

In practice, the materials used, as well as the contingent shapes and dimensions, may be any according to the requirements and to the state of the art.

The disclosures in Italian Patent Application No. 102018000010188 from which this application claims priority are incorporated herein by reference.

The invention claimed is:

1. A stem for a hip prosthesis, of the medium and/or long type, the stem comprising a stem body divided into a proximal region and a distal region, the proximal region forming an anterior wall, a posterior wall, a medial wall, and a lateral wall, wherein the anterior wall, the posterior wall, and the medial wall are provided at least partially with a porous structure with undercuts, said lateral wall being provided with a machining allowance that extends up to and includes the distal region, the lateral surface at the proximal region having a relief pattern that is configured to aid osseointegration and is obtained by partially removing the machining allowance, said distal region having a lateral wall that is completely free of machining allowance and is smooth.

2. The stem according to claim 1, wherein said stem is manufactured by additive manufacturing technology.

3. A method for providing a stem for a hip prosthesis, the method including the following steps:
providing a stem body having a proximal region and a distal region, by way of additive manufacturing technology,
providing said stem body with an anterior wall, a posterior wall, a medial wall, and a lateral wall,
wherein said anterior wall, said posterior wall and said medial wall have a porous structure with undercuts,
said lateral wall being provided with a machining allowance, and further comprising a step of removing said machining allowance from said lateral wall with machine tools until a smooth surface is achieved which lacks porosities at the distal region and has a relief pattern, adapted to assist osseointegration, at the proximal region.

4. The method according to claim 3, wherein said porous structure with undercuts of said anterior wall, said posterior wall, and said medial wall has pore dimensions of 300 to 1000 microns.

5. The method according to claim 3, wherein said stem body is made with a vertical extension.

6. The method according to claim 3, wherein said stem body is made with a horizontal extension.

7. The method according to claim 3, further comprising, prior to the step of removing said machining allowance, a step of HIP treatment.

8. The method according to claim 7, further comprising, after the step of removing said machining allowance, a step of shot peening.

\* \* \* \* \*